United States Patent
Kim

(10) Patent No.: US 8,223,333 B2
(45) Date of Patent: Jul. 17, 2012

(54) APPARATUS AND METHOD OF TESTING LIQUID CRYSTAL DISPLAY DEVICE

(75) Inventor: Tae Man Kim, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 246 days.

(21) Appl. No.: 12/591,892

(22) Filed: Dec. 3, 2009

(65) Prior Publication Data

US 2010/0157297 A1    Jun. 24, 2010

(30) Foreign Application Priority Data

Dec. 19, 2008    (KR) .................. 10-2008-0130284

(51) Int. Cl.
*G01J 4/00*    (2006.01)

(52) U.S. Cl. ........... 356/364; 349/187; 349/194; 349/61

(58) Field of Classification Search .................... 356/364
See application file for complete search history.

(56) References Cited

U.S. PATENT DOCUMENTS

2001/0021016 A1* 9/2001 Shimoda .................... 356/239.1
2007/0236686 A1* 10/2007 Kishioka ....................... 356/150

FOREIGN PATENT DOCUMENTS

JP    2004-309816    11/2004

* cited by examiner

*Primary Examiner* — Tarifur Chowdhury
*Assistant Examiner* — Abdullahi Nur
(74) *Attorney, Agent, or Firm* — McKenna Long & Aldridge LLP

(57)    ABSTRACT

A liquid crystal display (LCD) device testing apparatus that comprises a stage configured in an air-floating structure to feed a liquid crystal panel including combined upper and lower substrates, a backlight unit configured to include a light source for an emission of light disposed under the stage, a protective film formed to encompass and protect the light source, and a lower polarizing plate formed on the protective film to firstly polarize light emitted from the light source in a fixed axis direction, an upper polarizing plate separated from the upper surface of the liquid crystal panel by a fixed distance to secondarily polarize light from the liquid crystal panel in the fixed axis direction; and a charge couple device (CCD) camera disposed on the upper polarizing plate to scan an image on the liquid crystal panel using light secondarily polarized by the upper polarizing plate.

5 Claims, 2 Drawing Sheets

APPARATUS AND METHOD OF TESTING LIQUID CRYSTAL DISPLAY DEVICE

CROSS-REFERENCE TO RELATED APPLICATION

This application claims priority under 35 U.S.C. 119 to Korean Patent Application No. 10-2008-0130284, filed on Dec. 19, 2008, which is hereby incorporated by reference in its entirety.

BACKGROUND OF THE INVENTION

1. Field of the Disclosure

This disclosure relates to an apparatus for testing a liquid crystal display (LCD) device, and more particularly to an LCD device test apparatus and method capable of improving test efficiency.

2. Description of the Related Art

The LCD device is a display device that uses light modulation by a liquid crystal cell. The LCD device applies a voltage to the liquid crystal cell and changes its molecular alignment. This converts several optical properties such as birefractivity, light polarization, and light dispersion in the liquid crystal cell into a visual variation.

Such an LCD device can be smaller than a Brown tube (or cathode ray tube). As such, LCD devices are widely applied to office automation appliances such as personal and notebook computer monitors and photocopiers, as well as portable appliances such as mobile phones and pagers.

LCD devices can be classified into various types, including an active matrix type. Active matrix type LCD devices have been actively used in display devices. The process of manufacturing the active matrix type LCD device includes a substrate cleaning process, a substrate patterning process, an alignment film forming process, a substrate combining/liquid crystal injection process, and a mounting process.

More specifically, the substrate cleaning process removes contaminants on lower and upper substrates using a cleanser before and after the substrate patterning process. The substrate patterning process includes a lower substrate patterning process and an upper substrate patterning process.

The upper substrate includes color filters, a common electrode, a black matrix, and other components formed on it. The lower substrate includes signal lines, thin film transistors TFT, and pixel electrodes formed on it. The signal lines include data lines, gate lines, and others. Each of the thin film transistors is formed at an intersection of the gate and data lines. Each of the pixel electrodes is formed on a pixel region defined by means of the data and gate lines. The pixel electrodes are connected to the source electrodes of their respective thin film transistors.

During the alignment film forming process, the lower substrate is first coated with an alignment film and then rubbed. The liquid lower and upper substrates are completed through the substrate combining/liquid crystal injection process. The substrate combining/liquid crystal injection process includes a combining process of the upper and lower substrates, a liquid crystal injection process, an injection hole sealing process, a cleaning process, a grinding process, and a testing process, which are sequentially completed.

The liquid crystal panel as manufactured above can include a stain defect due to errors or carelessness during the above manufacturing process. This stain defect representing divergent brightness can be entirely or partially generated on the liquid crystal panel. Such a stain defect is detected by a macrography (or an examination with the naked eye). In other words, the detection of the stain defect is dependent upon the discernment of an inspector. As such, a poor LCD device with a dot defect, a line defect, and/or a stain defect is often distributed. In addition, it is difficult for an inspector to examine with the naked eye the large-sized LCD device of a recent trend.

BRIEF SUMMARY OF THE INVENTION

Accordingly, the present embodiments are directed to LCD device testing apparatus and method that substantially obviate one or more of the problems due to the limitations and disadvantages of the related art.

An object of the present embodiment is to provide LCD device testing apparatus and method that easily detect defects in a combined liquid crystal panel in order to improve test efficiency.

Additional features and advantages of the embodiments will be set forth in the description which follows, and in part will be apparent from the description, or may be learned by practice of the embodiments. The advantages of the embodiments will be realized and attained by the structure particularly pointed out in the written description and claims hereof as well as the appended drawings.

According to one general aspect of the present embodiment, an LCD device testing apparatus includes: a stage configured in an air-floating structure to feed a liquid crystal panel including combined upper and lower substrates; a backlight unit configured to include a light source for an emission of light disposed under the stage, a protective film formed to encompass and protect the light source, and a lower polarizing plate formed on the protective film to firstly polarize light emitted from the light source in a fixed axis direction; an upper polarizing plate separated from the upper surface of the liquid crystal panel by a fixed distance to secondarily polarize light from the liquid crystal panel in the fixed axis direction; and a CCD camera disposed on the upper polarizing plate to scan an image on the liquid crystal panel using light secondarily polarized by the upper polarizing plate, wherein the lower polarizing plate is configured to include first to fourth polarizing plates of different characteristics which are disposed on the upper, rear, left, and right surface of the protective film.

An LCD device testing method according to another aspect of the present embodiment uses an apparatus which includes a stage configured in a floating structure to feed a liquid crystal panel including combined upper and lower substrates; a backlight unit configured to include a light source for an emission of light disposed under the stage, a protective film formed to encompass and protect the light source, and a lower polarizing plate formed on the protective film to firstly polarize light emitted from the light source in a fixed axis direction; an upper polarizing plate separated from the upper surface of the liquid crystal panel by a fixed distance to secondarily polarize light from the liquid crystal panel in the fixed axis direction; and a CCD camera disposed on the upper polarizing plate to scan an image on the liquid crystal panel using light secondarily polarized by the upper polarizing plate. The LCD device testing method includes: enabling the light source to emit light; primarily polarizing light emitted from the light source by the lower polarizing plate in the fixed axis direction to apply this light to a liquid crystal panel disposed above the stage; secondarily polarizing light from the liquid crystal panel by the upper polarizing plate in the fixed axis direction; scanning an image of the liquid crystal panel with the CCD camera using secondarily polarized light; detecting a brightness difference between regions on the scanned image; and comparing the brightness difference with a reference value to determine whether or not the liquid crystal panel is desirable.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims. Nothing in this section should be taken as a limitation on those claims. Further aspects and advantages are discussed below in conjunction with the embodiments. It is to be understood that both the foregoing general description and the following detailed description of the present disclosure are exemplary and explanatory and are intended to provide further explanation of the disclosure as claimed.

BRIEF DESCRIPTION OF THE DRAWINGS

The accompanying drawings, which are included to provide a further understanding of the embodiments and are incorporated in and constitute a part of this application, illustrate embodiment(s) of the invention and together with the description serve to explain the disclosure. In the drawings.

DETAILED DESCRIPTION OF THE INVENTION

Figure 1:
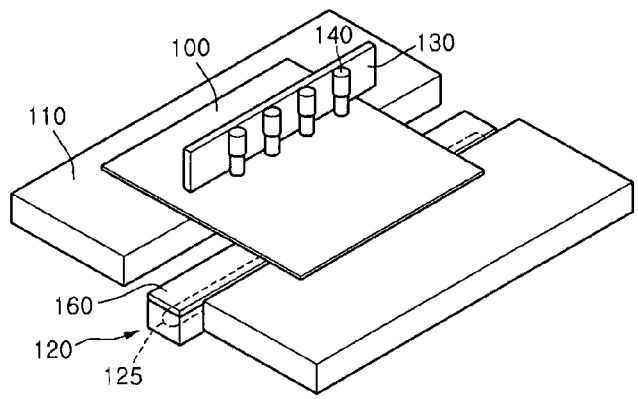
FIG. 1 is a view schematically showing an LCD device testing apparatus according to an embodiment of the present disclosure.

Reference will now be made in detail to the embodiments of the present disclosure, examples of which are illustrated in the accompanying drawings. These embodiments introduced hereinafter are provided as examples in order to convey their spirits to the ordinary skilled person in the art. Therefore, these embodiments might be embodied in a different shape, so are not limited to these embodiments described here. Also; the size and thickness of the device might be expressed to be exaggerated for the sake of convenience in the drawings. Wherever possible, the same reference numbers will be used throughout this disclosure including the drawings to refer to the same or like parts.

Figure 2:
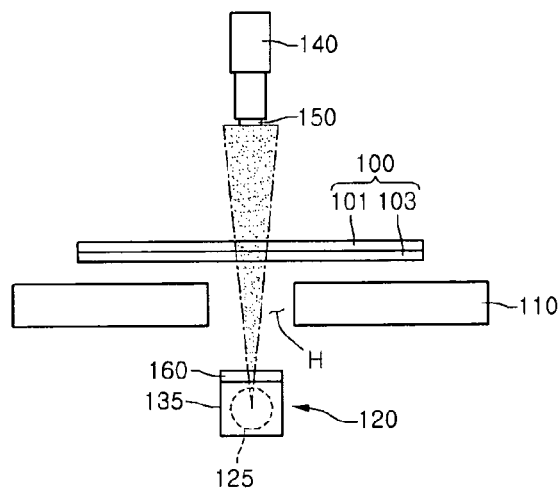
FIG. 2 is a cross-sectional view showing a sectional surface of the LCD device testing apparatus of FIG. 1.

FIG. 1 is a view schematically showing an LCD device testing apparatus according to an embodiment of the present disclosure. FIG. 2 is a cross-sectional view showing a sectional surface of the LCD device testing apparatus of FIG. 1.

Referring to FIGS. 1 and 2, an LCD device testing apparatus according to an embodiment of the present disclosure includes a stage 110 set up for the testing of an LCD device, a liquid crystal panel 100 disposed over the stage 110, a plurality of line scan cameras 140 separated from the liquid crystal panel 100 by a fixed distance, and a body unit 130 configured to support the line cameras 140. The LCD device testing apparatus further includes a backlight unit 120 under the stage 110, configured to irradiate light on the liquid crystal panel 100.

The liquid crystal panel 100 is disposed separately from the stage 110 by a fixed distance. To this end, the liquid crystal panel 100 floats in the air above the stage 110. The liquid crystal panel 100 may include an upper substrate 101 and a lower substrate 103 combined to each other. Such a liquid crystal panel may be moved on the stage 110 in an established direction.

The upper substrate 101 may include color filters, a common electrode, a black matrix, and other components formed on it. The lower substrate 103 may include signal lines, thin film transistors TFT, and pixel electrodes formed on it. The signal lines include data lines, gate lines, and others. Each of the thin film transistors is formed at an intersection of the gate and data lines. Each of the pixel electrodes is formed on a pixel region defined by means of the data and gate lines. The pixel electrodes are connected to the source electrodes of their respective thin film transistors.

Each of the line scan cameras 140 may be configured to include a charge coupled device (CCD). The CCD camera 140 photographs the liquid crystal panel 100 and automatically generates the coordinates of a defect position and/or a defect region. An upper polarizing plate 150 is disposed at the front of each CCD camera 140.

The backlight unit 120 includes a light source 125 configured to emit light, a protective film 135 formed to protect the light source 125, and a lower polarizing plate 160 provided on the protective film 135. The lower polarizing plate 160 includes first to fourth polarizing plates 160a to 160d which encompass the protective film 135. Alternatively, the lower polarizing plate 160 can be configured to include a polarizing film and a diffusion plate. In this case, light emitted from the light source 125 of the backlight unit 120 is polarized through the polarizing film in a fixed axis direction and then is diffused by means of the diffusion plate, thus being applied to the liquid crystal panel 100.

An operation of the LCD device testing apparatus, according to an embodiment of the present disclosure, for the testing of an LCD device will now be explained.

First, light is emitted from the light source 125 of the backlight unit 120. Light emitted from the light source 125 is first polarized in the fixed axis direction by the lower polarizing plate 160. Light first polarized in the fixed axis direction is applied to the liquid crystal panel 100 including the combined upper and lower substrates 101 and 103.

Then, light applied to the liquid crystal panel 100 is output in a variety of directions by an anisotropic refractive-index of the liquid crystal within the liquid crystal panel 100. Light output in the variety of direction is entered to the upper polarizing plate 150. The upper polarizing plate 150 secondarily polarizes the incident light in the fixed axis direction. The light secondarily polarized in the fixed axis direction by the upper polarizing plate 150 allows the CCD camera 140 to obtain an image of the liquid crystal panel 100.

The image of the liquid crystal panel 100 obtained by the CCD camera 140 can include regions of different brightnesses, i.e., portions in which a stain defect is presented and those where it is not. As such, the position of the defect on the liquid crystal panel 100 which includes the combined upper and lower substrate 101 and 103 is revealed by the brightness difference on the image of the liquid crystal panel 100, obtained through the CCD camera 140.

Figure 3:
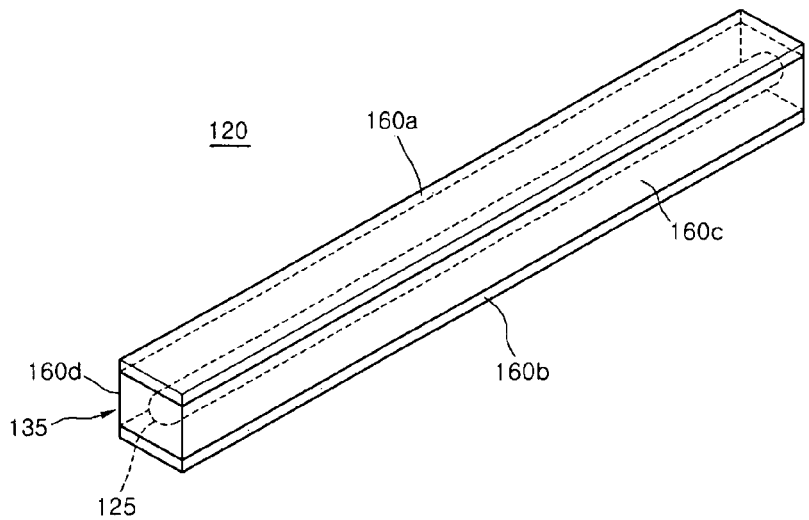
FIG. 3 is a view showing in detail a backlight unit shown in FIG. 1.

FIG. 3 is a view showing in detail the backlight unit shown in FIG. 1. The backlight unit 120 includes a light source 125 configured to emit light, a protective film 135 formed to encompass the light source 125, and first through fourth polarizing plates 160a~160d each provided on the outer surfaces of the protective film 135, as shown in FIGS. 1 and 3.

Among the first through fourth polarizing plates 160a~160d, the first and second polarizing plates 160a and 160b each provided to the upper and rear surfaces of the protective film 135 may be used in the liquid crystal panel 100 of an in-plane switching (IPS) mode. On the contrary, the third and fourth polarizing plates 160c and 160d each provided to the left and right side surfaces of the protective film 135 may be used in the liquid crystal panel 100 of a twisted nematic (TN) mode.

As such, the positions of the first and second polarizing plates 160a and 160b on the upper and rear surfaces of the protective film 135 can be exchanged with those of the third and fourth polarizing plates 160c and 160d according to whether the liquid crystal panel 100 disposed over (or above) the stage 110 is in the ISP mode or the TN mode. To this end, the backlight unit 120 further includes a rotation axis shaft (not shown) provided to rotate the first through fourth polarizing plates 160a-160d, and a motor (not shown) provided to drive the rotation axis shaft. The rotation axis shaft is combined with the protective film 135 and changes the locations of the first through fourth polarizing plates 160a~160d by a rotation torque from the motor.

More specifically, if the liquid crystal panel 100 disposed above (or over) the stage 110 is in the IPS mode, the motor responds to an operator's command and rotates the rotation axis shaft together with the protective film 135, in order to position the first and second polarizing plates 160a and 160b under the liquid crystal panel 100. On the contrary, when the liquid crystal panel 100 disposed above (or over) the stage 110 is in the TN mode, the third and fourth polarizing plates 160c and 160d are positioned under the liquid crystal panel 100, due to the rotation of the protective film 135 together with the rotation axis shaft by means of the motor, following an operator's command.

In this way, the positions of the first through fourth polarizing plates 160a-160d provided on the outer surfaces of the protective film 135 can be changed in accordance with the mode of the liquid crystal panel 100.

Figure 4:
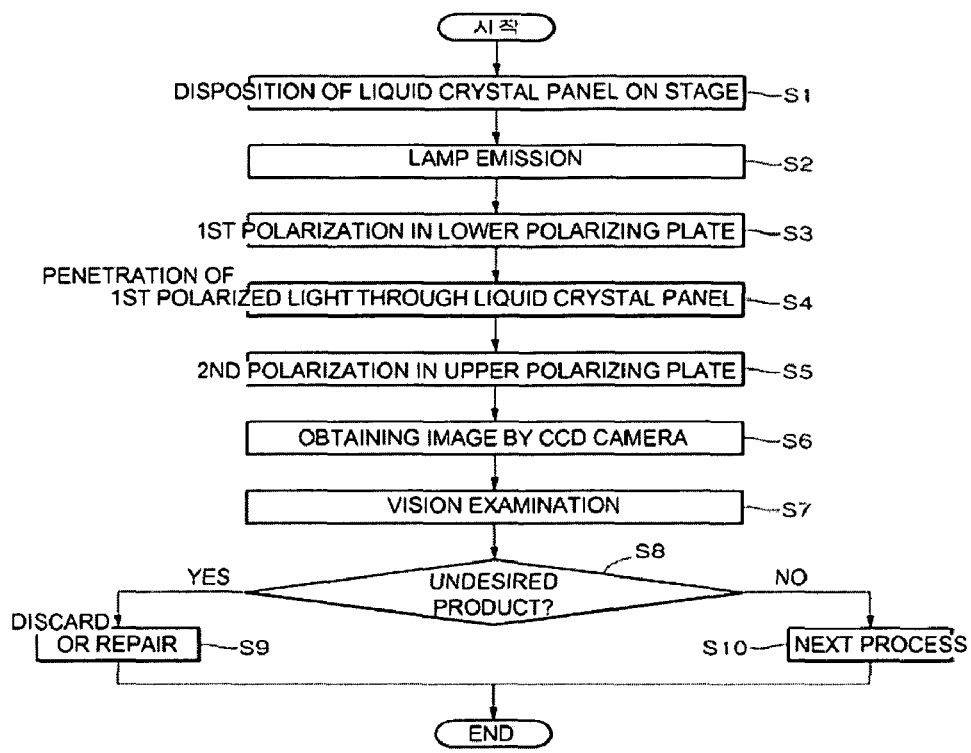
FIG. 4 is a flow chart explaining a testing process performed by an LCD device testing apparatus according to an embodiment of the present disclosure.

FIG. 4 is a flow chart explaining a testing process performed by an LCD device testing apparatus according to an embodiment of the present disclosure.

As shown in FIG. 4, the LCD device testing apparatus of the present embodiment disposes a liquid crystal panel 100 which includes the combined upper and lower substrates 101 and 103 above the stage 110 in a floating state (Step S1). The positions of the polarizing plates 160a-160d included in the backlight unit 120 are changed according to the mode of the liquid crystal panel 100 disposed above the stage 110. The light source 125 within the backlight unit 120 then emits light (Step S2).

Light emitted from the light source 125 is firstly polarized in the fixed axis direction by the lower polarizing plate 160 (Step S3). This light firstly polarized in the fixed axis direction is then applied to the liquid crystal panel 100 (Step S4). Light incident on the liquid crystal panel 100 is output in a variety of directions by an anisotropic refractive-index of the liquid crystal within the liquid crystal panel 100. This output of divergent light is entered into the upper polarizing plate 150 and light output from the liquid crystal panel 100 in the fixed axis direction is secondarily polarized (Step S5).

The secondarily polarized light allows the CCD camera 140 to scan the liquid crystal panel 100, thereby obtaining an image (Step S6). The obtained image is provided to a vision board (not shown) configured to perform a vision examination (Step S7). The vision board eliminates noises contained into the obtained image and improves the contrast of the noise-eliminated image. Also, the vision board determines whether or not the liquid crystal panel 100 is of poor quality, on the basis of a brightness difference generated between a normal portion and a defect portion of the contrast-improved image (Step S8).

If the brightness difference generated between the normal portion and the defect portion in the image is larger than a reference value (or a critical value), the vision board identifies the tested liquid crystal panel 100 as an undesired product that can be repaired or discarded (Step S9). On the contrary, when the brightness difference is smaller than the reference value (or the critical value), the vision board identifies the tested liquid crystal panel 100 as a superior product, thereby allowing the tested liquid crystal panel 100 to be applied to a following process (Step S10).

As described above, the LCD device testing apparatus and method of the present embodiments scan the liquid crystal panel, including the combined upper and lower substrates, with the CCD camera using light primarily and secondarily polarized by the lower and upper polarizing plates. Sequentially, the LCD device testing apparatus and method determine whether or not the liquid crystal panel is bad, on the basis of a scanned image of the liquid crystal panel. As such, the LCD device apparatus and method can greatly improve the test efficiency in comparison with the related art testing method which depends solely on the judgment of the naked eye.

In addition, the LCD device testing apparatus and method of the present embodiments enable the different lower-polarizing plates to be exchanged according to the mode of the liquid crystal panel. Therefore, the LCD device testing apparatus and method can test both of the IPS and TN mode liquid crystal panels. As a result, the test efficiency can be greatly improved.

Although the present disclosure has been limitedly explained regarding only the embodiments described above, it should be understood by the ordinary skilled person in the art that the present disclosure is not limited to these embodiments, but rather that various changes or modifications thereof are possible without departing from the spirit of the present disclosure. Accordingly, the scope of the present disclosure shall be determined only by the appended claims and their equivalents.

What is claimed is:

1. A liquid crystal display (LCD) device testing apparatus comprising:
   a stage configured in an air-floating structure to feed a liquid crystal panel including combined upper and lower substrates;
   a backlight unit configured to include a light source for an emission of light disposed under the stage, a protective film formed to encompass and protect the light source, and a lower polarizing plate formed on the protective film to firstly polarize light emitted from the light source in a fixed axis direction;
   an upper polarizing plate separated from the upper surface of the liquid crystal panel by a fixed distance to secondarily polarize light from the liquid crystal panel in the fixed axis direction; and
   a charge couple device (CCD) camera disposed on the upper polarizing plate to scan an image on the liquid crystal panel using light secondarily polarized by the upper polarizing plate,
   wherein the lower polarizing plate is configured to include first to fourth polarizing plates of different characteristics which are disposed on the upper, rear, left, and right surface of the protective film,
   wherein the first and second polarizing plates each provided to the upper and rear surfaces of the protective film are used in the liquid crystal panel of an in-plane switching mode, wherein the third and fourth polarizing plates each provided to the left and right side surfaces of the protective film are used in the liquid crystal panel of a twisted nematic mode, wherein the protective film is rotated according to a mode of the liquid crystal panel.

2. The LCD device testing apparatus according to claim 1, wherein the first and second polarizing plates are located under the liquid crystal panel when the mode of the liquid crystal panel is the in-plane switching mode, wherein the third and fourth polarizing plates are located under the liquid crystal panel when the mode of the liquid crystal panel is the twisted nematic mode.

3. The LCD device testing apparatus according to claim 1, wherein the backlight unit further includes a rotation axis shaft connected to the protective film to change the positions of the first to fourth polarizing plates according to a mode of the liquid crystal panel, and a motor configured to control the rotation axis shaft.

4. An LCD device testing method using an apparatus which includes a stage configured in a floating structure to feed a liquid crystal panel including combined upper and lower substrates; a backlight unit configured to include a light source for an emission of light disposed under the stage, a protective film formed to encompass and protect the light source, and a lower polarizing plate formed on the protective film to firstly polarize light emitted from the light source in a fixed axis direction; an upper polarizing plate separated from the upper surface of the liquid crystal panel by a fixed distance to secondarily polarize light from the liquid crystal panel in the fixed axis direction; and a CCD camera disposed on the upper polarizing plate to scan an image on the liquid crystal panel using light secondarily polarized by the upper polarizing plate, the method comprising:

enabling the light source to emit light;

primarily polarizing light emitted from the light source by the lower polarizing plate in the fixed axis direction to apply this light to a liquid crystal panel disposed above the stage;

secondarily polarizing light from the liquid crystal panel by the upper polarizing plate in the fixed axis direction;

scanning an image of the liquid crystal panel with the CCD camera using secondarily polarized light;

detecting a brightness difference between regions on the scanned image; and comparing the brightness difference with a reference value to determine whether or not the liquid crystal panel is desirable, wherein the lower polarizing plate is configured to include first to fourth polarizing plates of different characteristics which are disposed the upper, rear, left, and right surface of the protective film, wherein the first and second polarizing plates each provided to the upper and rear surfaces of the protective film are used in the liquid crystal panel of an in-plane switching mode, wherein the third and fourth polarizing plates each provided to the left and right side surfaces of the protective film are used in the liquid crystal panel of a twisted nematic mode, wherein the protective film is rotated according to a mode of the liquid crystal panel.

5. The LCD device testing method according to claim 4, wherein the first and second polarizing plates are located under the liquid crystal panel when the mode of the liquid crystal panel is the in-plane switching mode, and wherein the third and fourth polarizing plates are located under the liquid crystal panel when the mode of the liquid crystal panel is the twisted nematic mode.

* * * * *